United States Patent
Geistlich et al.

(10) Patent No.: US 6,713,085 B2
(45) Date of Patent: Mar. 30, 2004

(54) METHOD AND MEMBRANE FOR MUCOSA REGENERATION

(75) Inventors: Peter Geistlich, Stansstad (CH);
Lothar Schloesser, Darmstadt (DE);
Phillip J. Boyne, Loma Linda, CA (US)

(73) Assignee: Ed. Geistlich Soehne AG fuer Chemische Industrie (CH)

( * ) Notice: Subject to any disclaimer, the term of this patent is extended or adjusted under 35 U.S.C. 154(b) by 0 days.

(21) Appl. No.: 10/128,525

(22) Filed: Apr. 24, 2002

(65) Prior Publication Data
US 2002/0160036 A1 Oct. 31, 2002

Related U.S. Application Data
(60) Provisional application No. 60/286,531, filed on Apr. 27, 2001.

(51) Int. Cl.⁷ .................................................. A61K 9/70
(52) U.S. Cl. ........................................ 424/443; 424/402
(58) Field of Search ............................. 424/400, 435, 424/434, 422, 443, 484, 445, 446, 447, 448, 449, 402

(56) References Cited

U.S. PATENT DOCUMENTS

| | | | |
|---|---|---|---|
| 4,772,470 A | * | 9/1988 | Inoue et al. ............ 424/435 |
| 4,880,429 A | | 11/1989 | Stone |
| 5,162,430 A | | 11/1992 | Rhee et al. |
| 5,206,023 A | | 4/1993 | Hunziker |
| 5,413,597 A | | 5/1995 | Krajicek |
| 5,567,806 A | | 10/1996 | Abdul-Malak et al. |
| 5,759,190 A | | 6/1998 | Vibe-Hansen et al. |
| 5,837,278 A | | 11/1998 | Geistlich et al. |
| 5,989,269 A | | 11/1999 | Vibe-Hansen et al. |
| 6,120,514 A | | 9/2000 | Vibe-Hansen et al. |
| 6,153,292 A | | 11/2000 | Bell et al. |
| 6,221,109 B1 | | 4/2001 | Geistlich et al. |
| 6,283,980 B1 | | 9/2001 | Vibe-Hansen et al. |
| 6,352,558 B1 | | 3/2002 | Spector |

FOREIGN PATENT DOCUMENTS

| | | |
|---|---|---|
| FR | 2 679 778 A1 | 2/1993 |
| WO | WO 90/13302 A1 | 11/1990 |
| WO | WO 92/13565 A1 | 8/1992 |
| WO | WO 93/10722 A2 | 6/1993 |
| WO | WO 93/11723 A1 | 6/1993 |
| WO | WO 93/19168 A1 | 9/1993 |
| WO | WO 96/24310 A1 | 8/1996 |
| WO | WO 96/25961 A1 | 8/1996 |
| WO | WO 98/08469 A2 | 3/1998 |
| WO | WO 99/19005 A1 | 4/1999 |
| WO | WO 9960951 A1 * | 12/1999 ............ A61F/2/00 |
| WO | WO 01/15711 A1 | 3/2001 |

OTHER PUBLICATIONS

Breinan, H.A., et al., "Reparative Tissues in Articular Cartilage Defects in a Canne Model Treated by Microfracture", *Orthopaedic Research Society*, 1 page, 45th Annual Meeting, Anaheim, California; Feb. 1–4, 1999.

"Bio-Gide: Resorbable Bilayer Membrane for Bone Regeneration", *Geistilch Biomaterials*, 2 pp.

"Carticel (Autologous cultured chondrocytes): Get in the Game", *Genzyme Tissue Repair*, 9 pp., 1998.

Chondro-Gide: Collagen Membrane for Articular Cartilage Repair, *Geistlich Biomaterials*, 15 pages.

(List continued on next page.)

Primary Examiner—Thurman K. Page
Assistant Examiner—Robert M. Joynes
(74) *Attorney, Agent, or Firm*—Rothwell, Figg, Ernst & Manbeck, PC

(57) ABSTRACT

Healing of mucosa injury is promoted by applying thereto a membrane of purified collagen material derived from natural collagen-containing tissue.

9 Claims, 1 Drawing Sheet

OTHER PUBLICATIONS

Lee, C.R., et al., "Harvest and Selected Cartilage Repair Procedures Affect Mechanical and Biochemical Properties of Uninvolved Articular Cartilage in the Canine Knee", *Orthopaedic Research Society*, 45th Annual Meeting, Anaheim, California, Feb. 1–4, 1999.

Lee, C. R., et al., "The Contractile Behavior of Articular Chondrocytes in Collagen Matrices in Vitro", Dec. 4–6, 1998.

Mueller, S., et al., "Alpha–smooth Muscle Actin in Bovine Meniscus Cells Seeded in Type I and Type II Collagen–gag Matrices", *Orthopaedic Research Society*, 44th Annual Meeting, New Orleans, Louisiana, Mar. 16–19, 1998.

Mueller, S.M., et al., "α–Smooth Muscle Actin and Contractile Behavior of Bovine Meniscus Cells Seeded in Type 1 and Type II Collagen–GAG Matrices", *John Wiley & Sons, Inc. J Biomed. Mater. Res.*, vol. 45, 157–166, 1999.

Mutter, D., et al., "Biomaterial Supports for Colonic Wall Defect Healing", *Biomaterials*, vol. 17, No. 14, pp. 1411–1415 (1996).

Nehrer, S., et al., "Canine Chondrocytes Seeded in Type I and Type II Collagen Implants Investigated In Vitro", *John Wiley & Sons, Inc. J. Biomed Mater Res (Appl Biomater)*, 38:95–104, 1997.

Nehrer, S., et al., "Matrix Collagen Type and Pore Size Influence Behaviour of Seeded Canine Chondrocytes", *Biomaterials*, vol. 18, No. 11, pp. 769–776 (1997).

Nehrer, S., et al., "Characteristics of Articular Chondrocytes Seeded in Collagen Matrices in Vitro", *Tissue Engineering*, vol. 4, No. 2, pp. 175–183 (1998).

Nehrer, S., et al., "Chondrocyte–seeded Type I and Type II Collagen Implants Investigated In Vitro", *Fifth World Biomaterials Congress*, 1996, Toronto, Canada.

Nehrer, S., et al., "Autologous Chondrocyte–seeded Type I and Type II Collagen Matrices Implanted in a Chondral Defect in a Canine Model", *Orthopaedic Research Society*, 44th Annual Meeting, New Orleans, LA, Mar. 16–19, 1998.

Nehrer, H.A., et al., "Chondrocyte–seeded Type I and Type II Collagen Matrices Implanted in a Chrondral Defect in a Canine Model", *Dept. of Orthopedic Surgery*.

Pieper, J.S., et al., "Development of Tailor–made Collagen–glycosaminoglycan Matrices: EDC/NHS Crosslinking, and Ultrastructural Aspects", *Biomaterials*, vol. 21, pp. 581–593 (2000).

Schneider, T., et al., "Expression of α–Smooth Muscle Actin in Canine Intervertebral Disc Cells In Situ and in Collagen-GAG Matrices In Vitro", *J. Orthopaedic Research*, pp. 1–17 and Figs. 1–4.

Shultz–Torres, D., et al., "Tendon Cell Contraction of Collagen–GAG Matrices in Vitro: Effect of Cross–linking", *Soc. for Biomaterials*, Providence, Rhode Island, Apr. 28–May 2, 1999.

Stone, K., et al., "Regeneration of Meniscal Cartilage with Use of a Collagen Scaffold", *The Journal of Bone and Joint Surgery, Incorporated*, vol. 79–A, No. 12, 1997, pp. 1770–1777.

* cited by examiner

METHOD AND MEMBRANE FOR MUCOSA REGENERATION

CROSS-REFERENCE TO RELATED APPLICATIONS

This application claims benefit of Provisional Application No. 60/286,531, filed Apr. 27, 2001.

BACKGROUND OF THE INVENTION

1. Field of the Invention

The present invention relates generally to methods for regeneration of mucosa.

2. Discussion of the Background Art

The use of split thickness skin grafts and oral mucosal free grafts in vestibular deepening and other types of vestibuloplasty surgery in the oral cavity has been an established procedure for some time. In addition, the use of free mucosal grafts taken from the palate and from the buccal mucosa has been used in re-establishing attached mucosal surfaces in edentulous alveolar ridge areas particularly in conjunction with the use of root form implants.

While such grafting procedures are well established, the development of an effective alloplastic or xenogeniec substitute graft material for the reconstruction and regeneration of normal mucous membrane would bring about a much wider application of vestibuloplasty surgical procedures.

There remains a need in the art for improvements in promoting regeneration of mucosa in general and, in particular, following vestibuloplasty surgical procedures.

SUMMARY OF THE INVENTION

In accordance with the present invention, mucosa regeneration is promoted utilizing a membrane comprised of a purified collagen material derived from natural collagen-containing tissue.

DETAILED DESCRIPTION OF THE PREFERRED EMBODIMENT

The present invention provides a method for promoting regeneration of mucosa. While the method is described in connection with promoting regeneration of mucosa in the oral cavity following specific types of oral surgery, it will be appreciated that the method can be employed to promote regeneration of mucosa in any part of the body having damaged mucosal tissue.

In preferred embodiments, a method of promoting regeneration of mucosa includes the steps of covering the area to be treated with a patch comprised of a sheet of collagen membrane material, wherein the collagen membrane material is comprised of at least one layer having a smooth face and a fibrous face opposite the smooth face, the fibrous face allowing cell growth thereon, wherein the collagen membrane preferably further comprises a second layer predominantly of collagen II or a mixture of collagen I and III having an open sponge-like texture. The patch is fixed over a defect in the mucosa, preferably with sutures, and the mucosa is allowed to regenerate.

Figure 1:
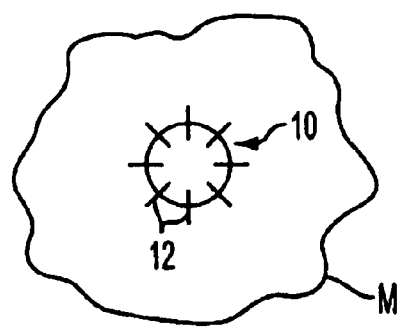
FIG. 1 is a plan view showing a patch of collagen membrane material covering an area of mucosa to be treated.

In accordance with the present invention, as shown in FIG. 1, a defect in a mucosal surface M is repaired by placing a patch 10 over the defect and securing the patch to margins of the mucosal surface around the defect. The patched area is then allowed to regenerate mucosa. In FIG. 1, the patch 10 is shown secured by sutures 12 to the mucosal surface M. Alternatively, the patch can be secured over the defect by adhesively bonding the patch to the surrounding host mucosa or other structures surrounding the area to be treated, for example, utilizing an organic glue as is known in the art, or any other suitable method.

The patch 10 is formed of a preparation comprising a collagen membrane with appropriate pliability to conform closely to the shape of the mucosal surface against which it is placed. In a preferred embodiment, the collagen membrane includes at least one collagen layer having sufficient strength to accommodate suturing to the mucosa and to protect the mucosal surface from trauma during the healing process.

Figure 2:
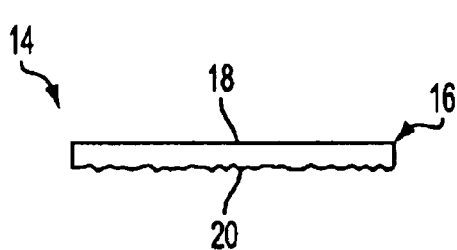
FIG. 2 is a sectional side view showing a membrane for use in accordance with the present invention.

A first embodiment of a collagen membrane for use as a patch in accordance with the present invention is shown in FIG. 2 at 14. The membrane 14 includes a single collagen layer 16 having a smooth face 18 on one side and a textured or fibrous face 20 on the other side opposite the smooth face. The smooth face 18 is preferably non-porous to provide mechanical protection, for example when eating. The fibrous face 20 is configured to allow cell growth thereon. In use, the smooth face preferably is oriented away from the area to be treated, and the fibrous face preferably is oriented toward the area to be treated.

In preferred embodiments, the collagen layer 16 is predominantly collagen I, collagen III or a mixture thereof. One suitable material for this layer is Biogide®, from Ed. Geistlich S öhne AG fur Chemische Industrie, the assignee of the present invention. The Biogide® material is described in U.S. Pat. No. 5,837,278, incorporated herein by reference.

Figure 3:
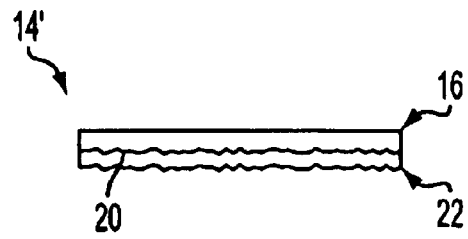
FIG. 3 is a sectional side view showing another membrane for use in accordance with the present invention.

FIG. 3 shows a multi-layer collagen membrane 14' that can be used as a patch in accordance with the present invention. This membrane includes a first collagen layer 16 as shown in FIG. 2, and further includes a second collagen layer 22 having an open sponge-like texture. The second collagen layer 22 is preferably attached to the fibrous face 20 of the first collagen layer 16 for placement against the mucosal surface to promote regeneration of mucosa. The second layer 22 can be formed of collagen I, II, III, IV, or VII any combination of these collagen types, but is preferably formed of predominantly collagen I, collagen II or a combination of collagen I and collagen III (e.g., 95% Type I collagen and 5% Type III collagen). The combination of the first and second layers 16 and 22 increases the thickness of the membrane 14' for easy handling and improved healing. The thickness of the membrane can vary depending upon application but will typically range from about 0.5 mm to about 5 mm, with a preferred range between about 2 mm and about 5 mm, and a thickness of about 3 mm being most preferred.

The first layer 16 in the embodiments shown in FIGS. 2 and 3 can be produced in a variety of ways including, but not limited to, the process steps described in U.S. Pat. No. 5,837,278; by de-airing and air-drying a slurry (film-like transparent membrane); by de-airing and vacuum-drying a slurry (film-like transparent membrane); or using compressed sponges. The first layer 16 can be made of collagen I, II, III or IV or combinations of these collagen types.

The second, sponge-like layer 22 in the embodiment shown in FIG. 3 is preferably a freeze-dryed collagen slurry. The second layer 22 can be made of collagen I, II, III, IV or VII or combinations of these collagen types. Preferably, the second layer is made of collagen I, collagen II or a mixture of collagen I and III.

The second collagen layer 22 may be formed from bovine or porcine material, and preferably is formed from porcine material.

In the embodiment shown in FIG. 3, the first and second membrane layers 16 and 22 can be connected to one another, or combined, in any suitable manner. Examples of three suitable methods of combination include: attaching the first membrane layer to the the second membrane layer with fibrin glue; attaching the first membrane layer to the second membrane layer using collagen slurry; or coating the first membrane layer with a collagen slurry of the desired collagen type for the second membrane layer, and then freeze-drying the combination.

If desired, growth factors such as EGF (Epidermal Growth Factor), IGF-1 (Insulin-like Growth Factor), β-FGF (Fibroblast Growth Factor), PDGF (Platelet-derived Growth Factor), TGF-β (Transforming Growth Factor) which promote mucosal regeneration, can be charged to the membrane, and/or added to the surface of the membrane that is placed against the mucosa.

EXAMPLE 1

Preparation of Patch (A) The first membrane layer is produced in accordance with the procedure described in WO 93/11723 (preparation of purified type I collagen, porcine skin), incorporated herein by reference. The final washed fibers are not freeze dried but the material is vacuum deaired an poured into a trace and dried in a laminar flow at room temperature.
(B) The second membrane layer is produced in accordance with the procedure described in WO 93/11723 (preparation of purified type I collagen, procine tendon). The final washed fibers are not freeze dried. They are acidificated again with hydrochloric acid to pH 2.9–3.2 to a dry content of 1.2–1.8%. This slurry is freeze dried to a sponge.
(C) The first and second membrane layers are combined by covering the first membrane layer on one side with the slurry pH 2.9–3.2 described above. Sponge on the slurry and freeze drying.

EXAMPLE 2

Preparation of Patch (A) The first membrane layer is produced in accordance with the procedure described in U.S. Pat. No. 5,837,278.
(B) The second membrane layer is produced in accordance with the procedure described in WO 99/19005, incorporated herein by reference, for the preparation of type II collagen slurry. Specifically, preparation of frozen cartilage from freshly slaughtered pigs to the washing step with cold water long enough for the pH value to rinse to pH 3–3.5. This material then is homogenized 5 times and diluted with water to get homogenous mass with a dry content of 0.5–2.0%.
(C) The first and second membrane layers are combined by pouring the slurry from the previous step on the first layer. After about 30 minutes, the combined product is freeze dried.

EXAMPLE 3

Preparation of Patch (A) The first membrane layer is produced in accordance with the procedure described in U.S. Pat. No. 5,837,278.
(B) The second membrane layer is produced by treating defatted rinds from pigs with 1 N sodium hydroxide solution, for about 4 hours at about 20° C., then treating with 1 N hydrochloric acid solution, for about 2 hours at about 20° C., and homogenizing as described in Example 2.
(C) The first and second membrane layers are combined by pouring the slurry from the previous step on the first layer. After about 30 minutes, the combined product is freeze dried.

EXAMPLE 4

Preparation of Patch (A) The first membrane layer is produced by drying the slurry gained in Example 3 through removal of the water with acetone, the acetone-wet product being pressed between two glass plates, and the acetones being removed with vacuum using a pressure of less than about 1 mBar, at about 35° C., for about 48 hours.
(B) The second membrane layer is produced by mixing the slurries resulting from the second steps in Examples 2 and 3 in equal quantities, and freeze drying the mixture to a sponge.
(C) The first and second membrane layers are combined by glueing with a fibrin glue.

EXAMPLE 5

Testing

The membrane material investigated was prepared from porcine Type I and Type III collagen manufactured in two layers. The deep or inner (second) layer of the collagen membrane has a roughened surface which is placed next to the host surgically prepared site to facilitate organization of the blood clot and to promote neoangiogenesis. The outer (first) layer of the bilayered collagen membrane has a smooth texture with appropriate elastic properties to accommodate suturing to the host mucosal margins and to protect the graft (patch) materials from oral trauma during the biodegrading and healing process. The sites utilized were all four oral mucosal quadrants of adult Papio anubis baboons. A 3 cm×2 cm in diameter elliptical excisional wound was made to the submucosa in the depth of the canine and premolar vestibulaes. This model supplied twelve specimens for vestibular deepening sites evaluation.

Additionally, an area of attached mucosa of the edentulous maxilla was utilized to determine how effective the material would be when used as a basis for regaining attached mucous membrane in edentulous alveolar ridge areas. An area 1½ cm×3 cm was dissected over the crest of the ridge extending from the buccal surface and crest of the ridge 1 cm over the palatal surface bilaterally in the three animals.

The membrane material was placed and secured to the margins of the host mucosal surface with a 4–0monofilament nylon interrupted sutures. (The total number of sutures for each collagen membrane placement varied from 10 to 16). The animals were given antibiotic coverage post-operatively for four post-operative days consisting of Penicillin, Procaine 150,000 units and Bicillin 150,000 units intramuscularly. The animals were placed on a regular diet and were allowed free movement in large cages with runs.

Biopsies of the vestibular surgical sites were made at the end of three weeks and six weeks. At three weeks, a biopsy on one side (2 quadrants) of each animal was made to extend from the superior native residual host mucosal surface across the surface of the membrane material to the opposite inferior graft host margin. The surfaces of the specimens were appropriately tagged with sutures for orientation for histologic examination. The biopsy area was closed with interrupted sutures and allowed to heal. Two quadrants of each animal were allowed to remain for six weeks at which time the entire area was excised and the mucosal surface undermined and brought together to obtain primary closure.

Biopsies of the attached mucosal area were similarly taken: one side at 3 weeks and one side of each animal at 6 weeks for a total of three specimens for each period.

The sutures in all cases were removed on the $14^{th}$ post-operative day. The clinical post-operative course of the animals was uneventful. There was no clinical evidence of inflammation or infection and no sloughing of the membrane material. The membrane remained in place and the margins indicated gradual re-epitheliazation from the host mucosal peripheral surfaces. Areas of residual membrane material were seen from the $2^{nd}$ through the $3^{rd}$ post-operative week clinically. At six weeks the entire surgical site had re-epithelized with a normal appearing mucosa.

The biopsies at the end of three weeks showed re-epitheliazation of the margins with normal retepeg formation. Degrading areas of collagen with the epithelium migrating over the surface of the membrane were seen. In the center portion of the membrane measuring approximately 0.5 cm×0.3 cm (from the original size of 3×2 cm) there was no re-epithelization.

In the 6-week specimens there was an excellent mucosal surface developed completely across the patched area with evidence of neoangiogensis submucosally and a normal stratified squamous epithelial formation in evidence with a complete excision and biopsy of the patched area. There was evidence of complete acceptance of the membrane material. Very small areas of residual collagen could be seen beneath the surface epithelium. Stains utilized were Mason's Trichrome and Hematoxyclin and Eosin.

Multiple sections were taken on the six week specimens to enable complete evaluation of the entire patched areas so that no residual membrane material would be undetected in the histologic examination process.

The patch, when placed in the posterior alveolar ridge and palatal maxillary surface, indicated a replacement of the membrane material similar to that seen in the vestibular depth type of test site. At three weeks there was evidence of residual membrane material which was in the center portion of the patched site. Fibroblasts and migrating epithelium could be seen from the peripheral margins of the patched site. In the six week specimens, new attached mucosa could be seen in all of the specimens on the palatal surface, on the alveolar ridge crest, and on the buccal aspect of the alveolar ridge. This indicated complete acceptance of the material and excellent re-reformation of attached mucosa.

The histologic appearance indicated that this material in the maxillary posterior area cold be used to re-establish attached mucosa in conjunction with root form implants although this area of efficacy was not specifically studied in this test.

The sites selected in the animals for vestibular grafting were in the maxillary and mandibular canine and premolar vestibular mucosal region. This area is particularly prone to trauma in the Papio anubis baboon during feeding and mastication and would serve as a stress-producing test site. Thus the material was placed in a situation which there was a high possibly of insult with resulting infection and dislodgement of the patch. This did not occur in any of the test sites and materials remained in place and were biodegraded by a very mild process of host cellular activity.

On the basis of these tests, it was concluded that use of a collagen membrane as a patch according to the present invention is an excellent substitute for autogenous soft tissue grafts. Some types of alloplastic or allogeneic surface dressings tend to produce a contracture of wound and scar formation. Also there is tendency for artificial skin surface dressings to either biodegrade and slough prematurely or to remain for prolonged period of time with a delayed inflammatory response. There was no evidence of either scarring or prolonged inflammatory response with the present invention. Neither was there any evidence of submucosal fibrosis which sometimes occurs in the use of surgical dressings.

Thus, it appears that this material could be used as a substitute for free mucosal grafts or split thickness skin grafts in maintaining the vestibular height and in the restoration of attached mucosa in the area of root form implants. Some of the apparent advantages of this method are that the membrane will (a) biodegrade without an adverse inflammatory response, (b) promote regeneration of the area with normal mucosa, and (c) be technically feasible in surgical manipulation and exhibit tolerance to suturing.

Since many modifications, variations and changes in detail may be made to the described embodiments, it is intended that all matter in the foregoing description and shown in the accompanying drawings be interpreted as illustrative and not in a limiting sense.

What is claimed is:

1. A method for promoting mucosa regeneration comprising covering an area of mucosa injury with a mucosa-regenerating preparation comprising a membrane comprised of a purified collagen material derived from natural collagen-containing tissue; said membrane comprising a barrier layer including an outer smooth collagen barrier face, and further including a fibrous collagen face opposite said smooth barrier face; said membrane comprising a multi-layer sheet of collagen membrane material which includes a matrix layer of collagen material adhered to said fibrous face; fixing the membrane over said area; and allowing said area to regenerate mucosa.

2. The method of claim 1 wherein said barrier layer is predominantly collagen I, collagen III or a mixture thereof.

3. The method of claim 1 wherein said matrix layer comprises collagen I, collagen II, collagen III, collagen IV, collagen VII or a combination thereof.

4. The method of claim 1 wherein said membrane has a thickness of about 0.5–5 mm.

5. The method of claim 3 wherein said matrix layer comprises predominantly collagen I.

6. The method of claim 3 wherein said matrix layer comprises predominantly collagen II.

7. The method of claim 1 wherein the membrane carries at least one mucosa-regenerating growth factor.

8. The method of claim 3 wherein said at least one growth factor is selected from the group consisting of Epidermal Growth Factor (EGF), Insulin-like Growth Factor (IGF-1), Fibroblast Growth Factor (-FGF), Platelet-derived Growth Factor (PDGF), Transforming Growth Factor (TGF- ), or a mixture thereof.

9. The method of claim 1 wherein said mucosa injury is an oral mucosa injury.

* * * * *